US007717946B2

(12) United States Patent
von Oepen et al.

(10) Patent No.: US 7,717,946 B2
(45) Date of Patent: May 18, 2010

(54) POLYMERIC PLATE BENDABLE WITHOUT THERMAL ENERGY AND METHODS OF MANUFACTURE

(75) Inventors: Randolf von Oepen, Los Altos Hills, CA (US); Alexander Tschakaloff, Pinneberg (DE)

(73) Assignee: Degima GmbH, Pinneberg (DE)

( * ) Notice: Subject to any disclaimer, the term of this patent is extended or adjusted under 35 U.S.C. 154(b) by 356 days.

(21) Appl. No.: 11/146,454

(22) Filed: Jun. 6, 2005

(65) Prior Publication Data

US 2005/0273104 A1 Dec. 8, 2005

Related U.S. Application Data

(60) Provisional application No. 60/577,638, filed on Jun. 7, 2004.

(51) Int. Cl.
*A61B 17/80* (2006.01)
(52) U.S. Cl. .................. 606/298; 264/323; 606/76; 606/907
(58) Field of Classification Search ............. 606/69–71, 606/76, 280–299, 902–907; 623/23.58, 23.59; 264/294; 156/156; 433/176
See application file for complete search history.

(56) References Cited

U.S. PATENT DOCUMENTS

| 5,690,631 | A | * | 11/1997 | Duncan et al. | ................. | 606/69 |
| 5,981,619 | A | * | 11/1999 | Shikinami et al. | ........... | 523/113 |
| 6,221,075 | B1 | | 4/2001 | Törmälä et al. | | |
| 6,352,667 | B1 | * | 3/2002 | English | ................. | 264/328.17 |
| 6,692,498 | B1 | * | 2/2004 | Niiranen et al. | ............... | 606/69 |
| 2001/0012940 | A1 | * | 8/2001 | Tunc | ........................... | 606/76 |
| 2003/0006533 | A1 | * | 1/2003 | Shikinami et al. | ........... | 264/323 |

FOREIGN PATENT DOCUMENTS

DE 29913390 9/1999
WO WO 90/07304 7/1990

(Continued)

OTHER PUBLICATIONS

João F. Mano et al., *Bioinert, biodegradable and injectable polymeric matrix composites for hard tissue replacement: state of the art and recent developments*, Composites Science and Technology 64 (2004) 789-817.

(Continued)

*Primary Examiner*—Thomas C Barrett
*Assistant Examiner*—James L. Swiger
(74) *Attorney, Agent, or Firm*—Workman Nydegger

(57) ABSTRACT

An implantable plate for providing support to a bone of a subject when affixed thereto includes a polymeric body of a biocompatible polymer having a desired amount of polymer molecule orientation in a first direction so that the plate can be bent to conform with a contour of the bone of the subject. The polymeric body includes a top surface, a bottom surface, and at least one fastener portion. The fastener portion includes a recess and a fastener hold that is configured for receiving a fastener when affixed to the bone of the subject. A method of manufacturing the implantable plate includes: (1) injection molding a biocompatible polymeric composition into a polymeric body within an injection mold; (2) removing the polymeric body from the injection mold; and (3) forming at least one fastener hole within polymeric body.

17 Claims, 10 Drawing Sheets

FOREIGN PATENT DOCUMENTS

WO     WO 2005/120370     12/2005

OTHER PUBLICATIONS

Christiane König et al., *Autosterilization of biodegradable implants by injection molding process*, printed from the website: http://www3.interscience.wiley.com/cgi-bin/abstract/44214/ABSTRACT on May 21, 2005, (2 pages).

C. Mauli Agrawal et al., *Biodegradable polymeric scaffolds for musculoskeletal tissue engineering*, Copyright 2001 John Wiley & Sons, Inc. (10 pages).

U.S. Appl. No. 60/577,638, filed Jun. 7, 2004, von Oepen, et al.

\* cited by examiner

POLYMERIC PLATE BENDABLE WITHOUT THERMAL ENERGY AND METHODS OF MANUFACTURE

CROSS-REFERENCE TO RELATED APPLICATIONS

This United States Patent Application claims the benefit of U.S. Provisional Patent Application Ser. No. 60/577,638, filed on Jun. 7, 2004, and entitled "Polymeric Plate Bendable Without Thermal Energy," with Randolf Von Oepen and Alexander Tschakaloff as inventors, which is hereby incorporated herein by reference. Additionally, this United States Patent Application cross-references other United States Patent Applications filed simultaneously herewith on Jun. 6, 2005, U.S. patent application Ser. No. 11/145,692, entitled "Fastener Having Torque Optimized Head" with Randolf Von Oepen as inventor Express Mail Label No. EV 607 585 498 US, and U.S. patent application Ser. No. 11/145,692, "Self Foreshortening Fastener" with Randolf Von Oepen as inventor, Express Mail Label No. EV 607 585 507 US. The disclosure of each of the foregoing cross-referenced United States Patent Applications is incorporated herein by reference.

BACKGROUND OF THE INVENTION

1. The Field of the Invention

The present invention relates generally to implantable plates for use bone repair. More particularly, the present invention relates to polymeric plates having polymer molecule orientation for providing strength and non-thermal bendability, and processes and systems for preparing such polymeric plates.

2. The Related Technology

Bones are a vital skeletal feature and provide the frame and structural support for holding associated muscles and other tissue. Additionally, bones, such as the skull bones and ribs, are responsible for protecting vital organs such as the brain, heart lungs, and the like. While bones are structurally strong, they tend to break for various reasons when subjected to excessive forces. Usually, the healing process includes a medical professional aligning the bones on each side of the break so that the regenerated bone material provides a structurally sound mended bone.

In addition to aligning the bone, various stabilizing techniques have been used to retain the broken bone in proper alignment during the healing process. Traditionally, casts have been used to stabilize minor breaks that do not need structural reinforcement at the bone. On the other hand, some complicated fractures or breaks can be susceptible to falling out of alignment during the healing process. As such, plates, pins, bone nails, wires, fasteners, and the like can be used to stabilize the broken bones or fix bone structures. Use of these kinds of structural reinforcement systems during healing have been known to provide bone regeneration and mending.

Due to excellent strength and stability profiles, metallic fasteners and plates have dominated the market for reinforcing breaks or fractures during healing. The most accepted metallic fasteners and plates are biocompatible titanium and/or titanium alloys; however, other types of metallic materials have also been used. Nevertheless, metallic fasteners and plates can be problematic and have some disadvantages.

One disadvantage of implanted metallic fasteners and plates arises from being treated as a foreign body, which sometimes requires the fasteners and plates to be removed. This can occur even if the metallic fastener and plate system is initially well tolerated. As such, the subsequent surgery to remove the metallic fastener and plate system can cause additional trauma to the patient, and adds additional costs to the health care system; especially when the patient has to be hospitalized after the procedure. Additionally, if the metallic fastener and plate system includes an iron component, the irons released from the metallic implant may be found in other organs, which can cause long-term problems.

Another major disadvantage of metallic fastener and plate systems arises from being much stronger than the bone being supported. As such, a broken bone that is fixed with a metallic fastener and plate system may not experience proper loading during the healing process. This is because the metallic repair system can carry a large portion of the load that is normally carried by the bone. As a result, the bone can become weaker over time when the metallic repair system is left in place. Accordingly, after removal of the metallic repair system, the repaired bone may be susceptible to fracturing around the region that was previously supported. Even though the metallic repair system provides structural reinforcement to the healing bone, the bone may develop decreased stability.

To overcome problems with metallic fasteners, fastener and plate repair systems have been fabricated out of various polymeric materials that can be configured into stiff and strong plates. In part, the vast array of different types of polymers have allowed for configuring the plate to be biocompatible. However, a major disadvantage of known polymeric repair systems arises during the implantation process. In contrast to metallic plates, polymeric plates typically cannot be plastically deformed in order to conform to the bone being repaired. In order to achieve adequate bending, heat is often required to soften the polymeric structure and adapt the plate to precisely fit with the geometry of the bone. Numerous processes for heating the plates to allow for such bending have been developed, which include hot air pistols, water baths, heat evolving pillows, laser energy, as well as many forms of heated tips or biopsy instruments. While it is possible to heat and bend a polymeric plate, a significant disadvantage arises due to the additional time and instruments required to implement the surgical procedure. Furthermore, systems such as water baths might face sterility problems.

Additionally, the processes typically used to form fastener holes in polymeric plates have caused anomalous features to develop, which are often sites for potential catastrophic failure. This is because during the injection molding processes pins extend through the mold cavity of the mold to form the fastener holes. As such, the polymeric melt being injected into the mold cavity has to flow around the pins, which have significant diameters in order to accommodate various fasteners. This can result in the melt separating into two melt flows that go around each pin, and each resulting flow has a cooled front portion. When the melt flows that have separated around the pins come into contact again, the significantly cooled front portions of each flow merely weld together instead of providing a homogenous union. The lines that form where the different flows or cooled front portions contact each other again are called joint lines or dwelt lines. Joint lines are a place of potential catastrophic failure, especially when bending the plate.

Therefore, it would be advantageous to have a polymeric plate that is bendable or deformable without heat in order to be contoured to the bone being repaired. Also, it would be beneficial to have a polymeric plate that is configured to provide good initial strength and stability, but also loses some mechanical strength over time so that the bone can self-repair to obtain proper strength and stability characteristics.

BRIEF SUMMARY OF THE INVENTION

Generally, an embodiment of the present invention includes a molded body for use in preparing an implantable plate. Such a molded body includes a top surface having a portion being configured to be oriented outward from the bone of the subject, and a bottom surface having a portion configured to be oriented inward toward the bone of the subject. Additionally, the body includes a recess defined by a recess surface, wherein the recess surface is adjacent to the top surface and extends into the body toward the bottom surface. Furthermore, the body can include a fastener hole template adjacent to a lower portion of the recess surface, wherein the fastener hole template is configured for being formed into a fastener hole that extends from the recess surface to the bottom surface. The hole template can be pre-drilled before a surgical procedure, or drilled during the surgical procedure.

Another embodiment of the present invention is an implantable plate for providing support to a bone of a subject when affixed thereto. Such a plate can be comprised of a biocompatible polymer having a desired amount of polymer molecule orientation in a first direction so that the plate can be bent to conform to a contour of the bone of the subject. Additionally, the plate includes at least one fastener portion at least partially defined by a portion of the top surface and a portion of the bottom surface. As such, each fastener portion includes a recess defined by a recess surface and a fastener hole that extends from a lower portion of the recess surface to the portion of the bottom surface. The fastener hole can be configured to receive a fastener when affixed to the bone of the subject.

Another embodiment of the present invention can be a method of manufacturing an implantable plate as described above. Such a method can include injection molding a biocompatible polymeric composition so as to form a polymeric body within an injection mold, wherein the polymeric body can include at least a portion configured to be an implantable plate at least partially defined by a top surface and a bottom surface. Additionally, the method can include removing the polymeric body from the injection mold and forming at least one fastener hole within the implantable plate portion.

These and other embodiments and features of the present invention will become more fully apparent from the following description and appended claims, or may be learned by the practice of the invention as set forth hereinafter.

BRIEF DESCRIPTION OF THE DRAWINGS

To further clarify the above and other advantages and features of the present invention, a more particular description of the invention will be rendered by reference to specific embodiments thereof which are illustrated in the appended drawings. It is appreciated that these drawings depict only typical embodiments of the invention and are therefore not to be considered limiting of its scope. The invention will be described and explained with additional specificity and detail through the use of the accompanying drawings in which.

DETAILED DESCRIPTION OF THE PREFERRED EMBODIMENTS

Figure 1:
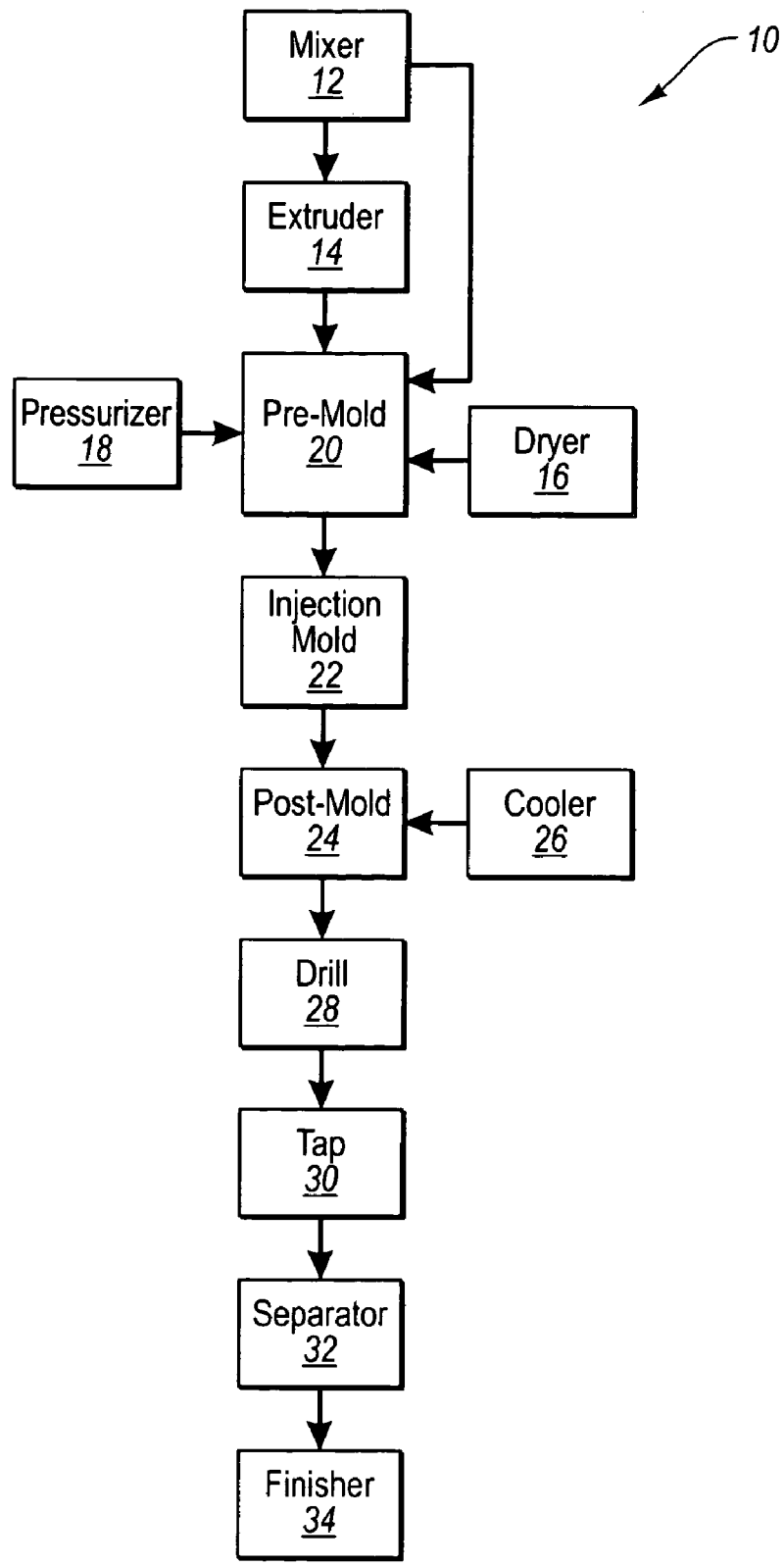
FIG. 1 is a block diagram illustrating an embodiment of a plate fabrication system in accordance with the present invention.

The present invention generally relates to implantable polymeric plates for bone repair, and associated methods of manufacture. The present invention also relates to implantable plates prepared from a biodegradable polymeric composition that have high initial strength after implant, but degrade slowly over time so as to weaken in strength.

I. Bendable Polymeric Plates and Methods of Manufacture

In general, it is known that articles manufactured from polymers can be configured to have various degrees of polymer chain orientation. Polymer chain orientation describes the amount of polymer macromolecules that are stretched or aligned in one direction. For example, applying a shear stress to a polymer composition can be used to create highly oriented polymeric articles that can be deformed without heat. However, various types of polymers that initially have high orientation may relax when implanted in the human body, which may cause the overall dimensions of the part to shrink or otherwise change dimensions. This can occur even though the body temperature is below the glass transition temperature of the polymeric material. Also, high levels of shear stress can also decrease orientation by causing the polymeric material to further increase in temperature so as to randomize the polymers before they are set. While it may be beneficial to incorporate biodegradable polymers into such parts, the biodegradation should be uniform and not cause the overall length, width, or thickness to shorten and/or straighten over time.

Accordingly, a polymeric plate that significantly shrinks and/or straightens after it has been implanted into the human body is not acceptable because of the problems associated with the forces applied to the mending bone. More particularly, high shrinkage in the direction of polymer molecule orientation tends to impart unfavorable stresses on the underlying bone. Also, the temperature of the body can induce a shape-memory process that straightens the plates so that they no longer conform to the shape of the mending bone. Such shrinkage and/or straightening of polymeric plates may be avoided by treating the plate at certain bending points with heat so as to increase the temperature above the softening point, glass transition temperature and/or melting point, thereby allowing the polymer molecule orientation to relax. On the other hand, such shrinkage and/or straightening can be achieved without the aid of heat by configuring the initial polymer molecule orientation to be in accordance with the present invention.

In one embodiment, a polymeric plate can be prepared by a process that provides a certain amount of polymer molecule orientation in order to allow the plate to be capable of bending without the use of heat. As such, it is possible to configure the plate to be capable of bending to angles of about thirty degrees or less. Also, the polymer molecule orientation can be configured to be low enough so as to avoid unfavorable shrinkage and/or straightening after implantation. Additionally, the polymer molecule orientation can be configured to avoid any shrinkage and/or straightening after being bent into a shape that conforms to the bone being reinforced. Moreover, the polymer molecule orientation can be configured to have enough directional orientation to provide strength and flexibility to the plate so that it will not break, fracture, or fatigue during the bending process.

In one embodiment, the plates can be fabricated by injection molding in order to achieve a desired amount of polymer molecule orientation. As such, injection molding can be performed to impart a shear stress to the polymer molecules that results in the desired amount of orientation, which is usually in the direction of the flow within the mold. As such, the runners, runner network, flow dividers, cold wells, gate regions, gates, mold cavity orientation, vents, mold temperature, polymer composition, and flow rates can be manipulated and changed to achieve the desired amount of polymer molecule orientation.

In one embodiment, a polymeric plate can be prepared by a process that includes optimizing the level of polymeric molecule orientation. As such, optimizing the level of polymeric molecule orientation can be performed in order to impart mechanical stability and bendability to the polymeric plate. By optimizing the injection molding conditions (e.g., polymer composition, mold configuration, polymer melt temperature, flow rates, gate configuration, shear stress, etc.), the process can provide a plate that can be bent to a certain extent, while avoiding a plate that will undergo unfavorable shrinkage and/or straightening. Furthermore, optimizing the injection molding conditions can avoid the formation of unfavorable joint lines because they are a potential place of catastrophic failure.

In one embodiment, a fabrication process provides increased plate stability and bendability by including a combination of injection molding and mechanically drilling the fastener holes. The geometry and composition of the plate can be formed during the injection molding process, which conforms to the shape of the cavity and polymers injected therein. The fastener holes are then mechanically drilled into the plate after being injection molded. When the fastener holes are drilled after injection molding, joint lines can be avoided. In part, this is because the shear stresses in the longitudinal flow direction within of the plate are not disturbed by the presence of pins or other flow altering features.

Additionally, the injection molding process can be configured to include a gate that provides the desired amount of polymer molecule orientation. More particularly, the gate within the injection mold can be adapted to orient the molecules by the shear stresses that are imparted to the polymeric melt when the injection mold cavity is being filled. A smaller gate can provide a high shear stress and result in high polymer molecule orientation; however, a gate that is too small can increase the shear stress past a favorable point and result in increased temperatures and randomized polymer orientations. Also, larger gate can reduce the shear stress and result in low polymer molecule orientation. Accordingly, the size of the gate can be modulated between small and large gates to optimize the polymer molecule orientation without unfavorably randomizing the polymers. Other factors that can be modulated in order to alter the polymer molecule orientation include, for example, melt temperature, mold temperature, injection rate, mold geometry, and the like.

In accordance with the foregoing, various polymeric plate fabrication parameters can be balanced so as to provide a plate that may be tested in a 37° C. water solution in order to mimic implantation into the human body. As such, the resulting plate can be configured and fabricated to have less than 5% shrinkage by volume or weight over a period of 10 days after being placed n a 37° C. bath.

II. Polymeric Compositions

Various types of polymers can be employed in preparing bendable polymeric plates in accordance with the present invention. The polymers can include a wide range of biocompatible materials that can be implanted within body of a living animal, such as a human, dog, cat, horse, cow, and the like. Additionally, the polymers can be combined and blended in order to achieve compositions that have high initial strengths, bendability, and can degrade within a living body over time.

In one embodiment, a polymer composition for use in injection molding a biocompatible plate can include at least one biodegradable polymer. For example, the biodegradable polymer composition can include at least one of poly(alpha-hydroxy esters), polylactic acids, polylactides, poly-L-lactide, poly-DL-lactide, poly-L-lactide-co-DL-lactide, polyglycolic acids, polyglycolide, polylactic-co-glycolic acids, polyglycolide-co-lactide, polyglycolide-co-DL-lactide, polyglycolide-co-L-lactide, polyanhydrides, polyanhydride-co-imides, polyesters, polyorthoesters, polycaprolactones, polyesters, polyanydrides, polyphosphazenes, polyester amides, polyester urethanes, polycarbonates, polytrimethylene carbonates, polyglycolide-co-trimethylene carbonates, poly(PBA-carbonates), polyfumarates, polypropylene fumarate, poly(p-dioxanone), polyhydroxyalkanoates, polyamino acids, poly-L-tyrosines, poly(beta-hydroxybutyrate), polyhydroxybutyrate-hydroxyvaleric acids, combinations thereof, or the like. Additionally, these polymers can be used at a wide range of molecular weights, which can range from less than about 25,000 MW to over 1,000,000 MW. More particularly, the molecular weight can vary depending on the type of polymer, initial strength, plate bendability, degradation rate, and the like. Additional information on the tensile strength, tensile modulus, flexural modulus, and elongations at yield and at break of various biocompatible and biodegradable polymers can be found with Engelberg and Kohn; Physico-mechanical Properties of Degradable Polymers Used in Medical Applications: A Comparative Study; *Biomaterials;* 1991; 12:292-304, which is incorporated herein by reference.

In one embodiment, a polymer composition for use in injection molding a biocompatible plate can include at least one inert polymer. For example, the inert polymer can include at least one of high-density polyethylenes, ultra-high-density polyethylenes, low-density polyethylenes, polypropylenes, polyacrylates, polymethylmethacrylates, polyethylmethacrylates, polysulfones, polyetheretherketones, polytetrafluoroethylenes, polyurethanes, polystyrenes, polystyrene-co-butadienes, epoxies, and the like. Such inert polymers can be used at a wide range of molecular weights in order to impart various mechanical strengths and bendabilty to the polymeric plate.

In one embodiment, the polymer composition for use in injection molding a biocompatible plate can include at least one natural polymer that can be derived from a natural source. Natural polymers can include polysaccharides, proteins, and the like. Examples of some suitable polysaccharides include methylhydroxyethylcellulose, hydroxymethylethylcellulose, carboxymethylcellulose, methylcellulose, ethylcellulose, hydroxyethylcellulose, hydroxyethylpropylcellulose, amylopectin, amylose, seagel, starches, starch acetates, starch hydroxyethyl ethers, ionic starches, long-chain alkylstarches, dextrins, amine starches, phosphate starches, and dialdehyde starches, alginic acid, phycocolloids, agar, gum arabic, guar gum, locust bean gum, gum karaya, gum tragacanth, and the like. Examples of some proteinaceous materials include collagens, caseins, and the like. Moreover, these natural polymers can also impart biodegradable characteristics to the plate.

In one embodiment, the biodegradable polymers can be reinforced with fibers comprised of magnesium, wherein such fibers can significant strength the plates. For example, short fibers, which are added to the polymer during the injection molding process, can be oriented in the direction of the flow so as to significantly improve the mechanical properties, such as strength and the plate's ability to bend. Additionally, the magnesium fibers can be pretreated with corona plasma or other well-known method to improve the interface between the polymers and fiber. Since pure magnesium can be highly reactive with water or body fluids, the polymer matrix can act as a shield and protect against fast degradation and magnesium reactions. It can also be understood that optionally the plate can be formed completely from magnesium and subsequently coated with a polymer coating to shield and protect against fast degradation.

In one embodiment, short fibers of biodegradable micro or nano-porous silicon materials, biodegradable ceramics, organic materials can be added to the polymer. The short fibers, which are added to the polymer during the injection molding process, can be oriented in the direction of the flow and significantly improve the mechanical properties, such as strength and the plate's ability to bend, of the resulting plate. Optionally, these degradable fibers can be pretreated with corona plasma or other well-known method to improve the interface between the polymer matrix and the fiber. Also, the rate of fiber biodegradation can be slowed by being encapsulated within the polymer matrix.

The addition of fibers into the implantable plate can improve many of the mechanical or strength characteristics of the implantable plate. In part, this can arise from the nature of the fibers, and/or being oriented with the polymer molecules. For example, the fibers can increase the Young's modulus, increase the strength, and decrease the shrinkage.

In one embodiment, the biodegradable polymers, inert polymers, natural polymers, magnesium fibers, and/or porous silicon fibers can be prepared into a polymeric blend that is comprised of different types of polymers and materials. As such, a polymeric blend can be configured to achieve injection moldability, polymer molecule orientation, high initial strength, and bendability. Moreover, the biodegradable polymers and/or natural polymers can be blended in order to achieve biodegradable plates that can degrade over time after being implanted.

In another embodiment, the plate can be fabricated from biodegradable micro or nano-porous silicon materials, biodegradable ceramics, or organic materials. Optionally, the plate made from one or more of these materials and ceramics can be coated or covered with a polymer or polymer matrix.

In yet another embodiment, the biodegradable polymers of the plate can be admixed with a drug for being delivered into the body after implantation. This can include mixing a drug into the polymer composition before being injection molded, or applying a drug-containing polymer coating onto the implantable plate. In any event, a portion of the implantable plate, either the bulk biodegradable polymer or a biodegradable coating can be configured to deliver drugs into the body after being implanted. Accordingly, any drug can be included into the implantable plate, especially analgesics, anti-inflammatory, anti-microbial, and like drugs.

III. Implantable Polymeric Plate Fabrication System and Process

In one embodiment, a fabrication system and process can be employed to prepare implantable plates having features in accordance with the present invention. Such a fabrication system includes the use of an injection mold configured to prepare polymeric implantable plates having the characteristics described herein, and the use of a drilling system to form faster holes in the implantable plates. An exemplary plate fabrication system and process is described in more detail below.

FIG. 1 is a schematic diagram illustrating an embodiment of a plate fabrication system 10 in accordance with the present invention. In general, the plate fabrication system 10 is configured to yield an implantable plate for structurally reinforcing a bone of a subject when affixed thereto. The plate fabrication system 10 can include a mixer 12 configured to receive polymeric materials, such as biodegradable and/or inert polymeric materials, in order to form a substantially homogenous polymeric composition. Additionally, the mixer 12 can be configured to receive other types of polymeric materials, plasticizers, rheology-modifying agents, fillers, and the like in order to provide various other characteristics to a polymeric plate fabricated with the plate fabrication system 10.

Optionally, the plate fabrication system 10 can include an extruder 14. As such, the polymeric composition mixed and formulated within the mixer 12 can, be supplied into the extruder 14 for further mixing, compacting, heating, and/or extruding. The extruder 14 can be a single screw extruder, double screw extruder, or piston-type extruder. Additionally, the extruder 14 can include heating elements in order to take advantage of the thermoplastic characteristics of some embodiments of the polymeric composition and heat the composition past its softening point, melting point, and/or glass-transition temperature. In any event, the extruder 14 can extrude the composition through a die head to an extrudate of any shape, which can optionally be pelleted before injection molding.

After being extruded from the extruder 14 or mixed within the mixer 12, the polymeric composition can be introduced into a pre-mold 20. The pre-mold 20 is a compartment, container, tube, conduit, injection line, hopper, or the like in fluid communication with the injection mold 22 that can hold the polymeric material before being injection molded. Alternatively, the composition can be provided directly into the injection mold from the extruder 14 or mixer 12.

Additionally, a dryer 16 can dry the polymeric material while in the pre-mold 20. Sometime the polymeric material can absorb moisture during processing, wherein the moisture can be counter-effective to a resulting plate; especially when a biodegradable polymer, which can cause the plate to prematurely degrade. As such, the dryer 16, can be configured to remove moisture from the polymeric material.

Additionally, a pressurizer 18 can pressurize the pre-mold 20 so that polymeric composition can be injected into the injection mold 22 under high pressure. In any event, dryer 16 and pressurizer 18 may be optional because the pre-mold 20 and/or the injection mold 22 may be outfitted with such components in order to provide these functionalities. Also, various other well-known injection molding equipment may be utilized in conjunction with the pre-mold 20 so as to prepare the polymeric composition for injection molding.

In any event, the polymeric composition can be injected into the injection mold 22 in order to prepare the implantable plate. Usually, the process includes injecting the polymeric composition under high pressure and/or heat so that the composition can flow through the various pathways and compartments within an injection mold. This allows the polymeric composition to be injection molded into an article of manufacture such as the implantable plate, as described in further detail below.

Optionally, the molded article prepared from the polymeric composition can be removed from the injection mold 22 and moved into a post-mold 24. Such a post-mold can be any component within an injection molding system that receives the molded article in a heated or otherwise freshly molded form so that it can be conditioned for further processing. Alternatively, the post-mold can be the state of the mold body containing the molded article after injection molding is complete. Accordingly, the post-mold 24 can be coupled with, or in fluid communication with, a cooler 26 to provide cool air or other cooling fluid for decreasing the temperature of the molded article. Cooling the molded article can increase form-stability and ease of handling. Additionally, the post-mold 24 can include various other well-known components in injection molding systems in order to prepare a molded article for further processing. Alternatively, the molded article can be removed from the mold and flushed with an inert gas. This can aid in conditioning the polymer for further processing or implantation.

It will be understood that the functionality of one or more of the injection mold 22, the post-mold 24, and the cooler 26 can optionally be combined when a cooled injection mold 22 is used to create the molded article. For instance, a water, air, or fluid cooled injection mold 22 can be used to fabricate the molded article of the present invention.

After being sufficiently prepared for further processing, the molded article can be introduced into the drilling apparatus 28. The drilling apparatus 28 can be configured to include various mechanisms and assemblies in order to align the implantable plate in the proper orientation so that fastener holes can be formed. The drilling apparatus 28 can form the fastener holes by drilling, milling, stamping, punching, laser machining, and the like. In any event, the drilling apparatus 28 can be configured to precisely drill holes within the plates.

Optionally, the molded article can be processed with an optional tap assembly 30. Such a tap assembly 30 can include taps in order to form threads on the inner wall of any of the holes drilled in the plate. As such, the holes in the implantable plate can be threaded so as to interact or interlock with the threads of a screw, bolt or other fastener when securing the implantable plate to the bone of the subject. The tap assembly 30 can be optional because some embodiments of the present invention do not require such threaded holes in order for proper functionality.

Before or after the fastener holes are formed, the plate can be introduced into a separator assembly 32. Molded bodies typically include various irregularities in the external surface that arise from the injection molding system and mold bodies. Also, when cold runner injection molding is utilized, the molded body can include runners, vents, junctions, dividers, cold wells, and other injection molding side products that need to be removed from the plate before it can be utilized for its designed function (i.e., implantation and bone affixation). As such, the separator assembly 32 can be configured with mechanic features in order to receive the molded body, and remove the various excess polymeric materials from the plate. Accordingly, the separator assembly 32 can use cutters, stamps, punches, and/or other techniques to remove the extra material away from the implantable plate. Thus, after being processed through the separator assembly 32, the polymeric plate can be substantially shaped for implantation.

Additionally, the polymeric plate outfitted with fastener holes can be introduced into a finishing assembly 34. Such a finishing assembly 34 can be configured to finish the plate and place it in the proper configuration for being implanted and affixed to a bone of a subject. This can include applying extra coatings of material onto of the polymeric plate, re-surfacing some of the edges of the plate, or other well-known finishing techniques for enabling implantation.

While general features of a plate fabrication system 10 have been described in connection with injection molding, various other similar processes or techniques can be utilized in order to prepare the implantable plate in accordance with the present invention. Accordingly, various modifications to the foregoing process can be made to include any well-known injection molding equipment, systems, and processes. Additionally, some of the foregoing components within such a plate fabrication system 10 will be described in more detail below.

IV. Injection Molding

In one embodiment of the present invention, the system and process for preparing an implantable plate employs an injection molding system. An injection molding system has the benefits of being configured to include certain features for obtaining proper polymer molecule orientation in order to achieve implantable plates having the strength and flexibility as described herein. An exemplary injection mold is described in more detail below.

Figure 2:
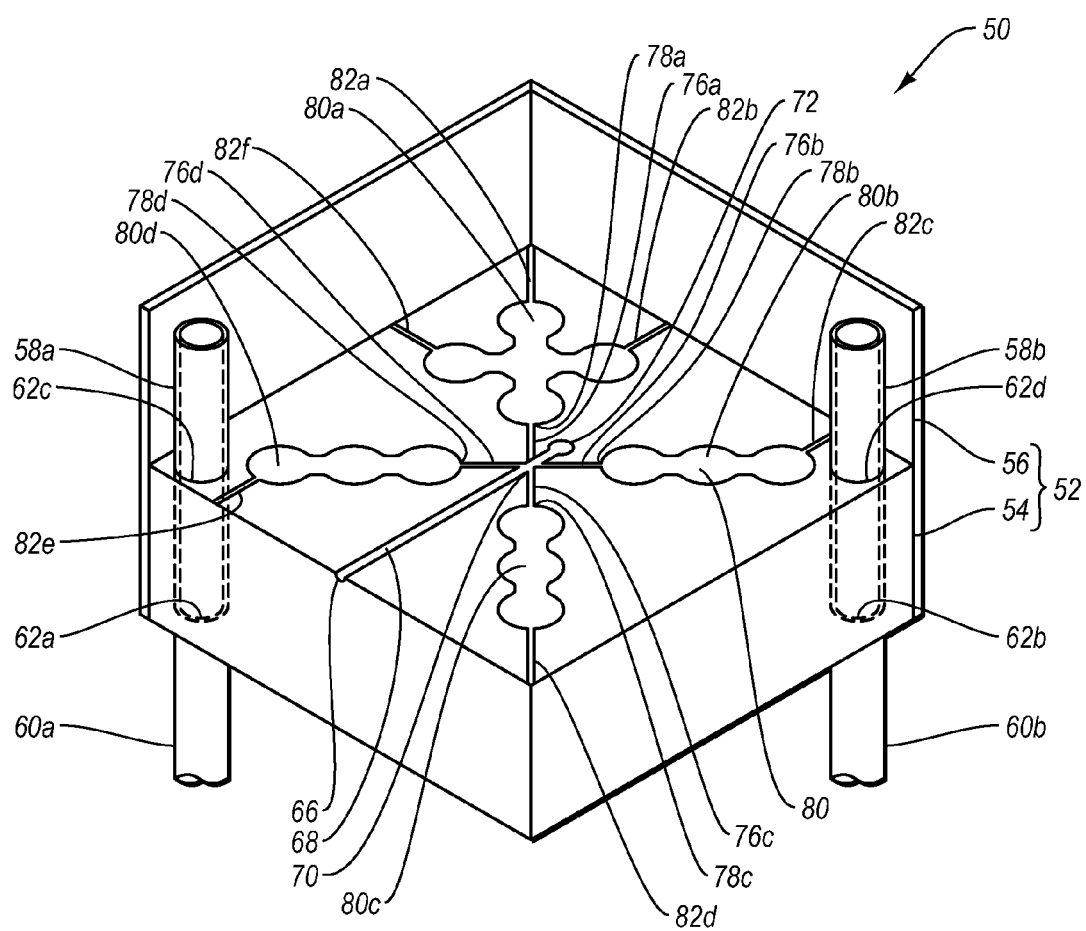
FIG. 2 is a schematic diagram illustrating an embodiment of an injection molding apparatus in accordance with the present invention.

FIG. 2 is a schematic diagram illustrating an embodiment of an injection mold apparatus 50. The injection mold 50 can be configured to be usable as the injection mold 22 of FIG. 1. Accordingly, the injection mold 50 can be capable of forming molded bodies from thermoplastic materials that have been processed and/or conditioned for proper injection molding. The injection mold 50 includes various components and features in order to form an injection molded article such as the implantable plate.

Accordingly, the injection mold 50 includes a mold 52. The mold 52 can be comprised of a first mold body 54 and a second mold body 56. The first mold body 54 can be configured to be aligned and compatible with the second mold body 56. This allows the first mold body 54 and the second mold body 56 to come together and form a mold cavity 80 in the shape of the molded article. As such, each of the first mold body 54 and second mold body 56 includes various components and features that cooperate for functioning as the injection mold 50.

The mold 52 includes pin holes 58*a-b* to hold pins 60*a-b* for enabling opening and closing. As illustrated, the pin holes 58*a-b* extend through the first mold body 54 and into the second mold body 56. In order to function, the pin 60*a-b* can be inserted into the pin aperture 62*a-b* and through second mold body 56 before being inserted through pin aperture 62*c-d* of first mold body 54. This configuration allows first mold body 54 and second mold body 56 to combine into the mold 52, and the separation of first mold body 54 from second mold body 56 in order to be able to extract molded article therefrom. A mechanical feature (not shown) operates in conjunction with pins 60*a-b*, first mold body 54, and second mold body 56 for facilitating the opening and closing of the mold 52 for injection molding and extracting the injection molded article therefrom. Moreover, various types and configurations of mechanical features are well known in the art and are considered to be included within the scope of the present invention.

Additionally, the mold 52 includes a runner inlet 66. For example, a runner inlet 66 can be present in a variety of dimensions such as a diameter or cross-sectional length of about 2 mm to about 5 mm or in other configurations from about 3 mm to about 4 mm. As used herein, the term "cross-sectional length" is meant to refer to the diameter of a circular cross-sectional area or width of polygonal cross-sectional area. The runner inlet 66 can be configured and oriented to receive a flow of thermoplastic polymer into the runner 68 or a runner network. Runners 66 can also range in dimensions, and can be present with a diameter or cross-sectional length of about 1 mm to about 3 mm. Typically, a major runner 68 can be about 2 mm to about 3 mm, wherein a runner that feeds a cavity can range from about 0.75 mm to about 1.5 mm. In other configurations, the diameter or cross-sectional length of a feeding runner can range from about 1 mm to about 1.2 mm or be about 1.1 mm. The runner 68 provides a conduit for the thermoplastic flow of polymeric materials to be properly distributed throughout the mold 52 and more specifically, into the mold cavity 80. The runner 68 can be configured to either be a cold runner or a hot runner.

When a cold runner, a polymeric runner can be formed as part of the molded article, which is cooled and injected with the molded plate. In a hot runner mold, the runner 68 is situated internally in the mold and kept at a temperature above the softening or melting point of the polymeric composition. As such, runner scrap can be eliminated or reduced with use of a hot runner.

In one embodiment, the runner 68 can provide a flow of thermoplastic polymers into multiple cavities 80a-d. In this instance, mold 52 includes a divider 70 to separate the flow. Often, the divider 70 can be placed at a junction of multiple runners 68 so that the flow of polymeric material can be directed towards any of the various cavities 80a-d within the mold 52. Additionally, the divider 70 can be in communication with a cold well 72. Such a cold well 72 can be a pocket or a cavity within the mold 52 that allows for the front or cooled portion of the thermoplastic melt to be trapped and not processed into the molded article. As such, providing for various cold wells 72 at the end of various runners 68 can provide a space for the somewhat harder, cooler, or solidified polymeric material to be trapped.

In one embodiment, the mold 52 includes a gate region 76a-d. As such, each cavity 80a-d includes a gate region 76a-d between the cavity and the corresponding runner 68 or divider 70 so that the polymeric material flows through a gate region 76a-d. A gate region 76a-d can be configured to constrict or expand the thermoplastic flow. For example, a gate region 76a-d can be designed to constrict the flow from a large runner to a small gate 78a-d, wherein the angle of constriction can be about 10 degrees to about 90 degrees. In other configurations, the angle of constriction can range from about 30 degrees to about 75 degrees or be about 60 degrees.

Additionally, each gate region 76a-d includes a gate 78a-d. Each gate 78a-d can be configured to impart some shear stress to the thermoplastic flow as it enters the cavity 80a-d. With that said, each gate 78 a-d can be configured for each type of polymer flow in order to provide the proper polymer molecule orientation to the molded article. The gate 78a-d can have various shapes, sizes, and dimensions to provide properly aligned or oriented polymers in the molded articles. For example, the gate. 78a-d can be configured to have a diameter or cross-sectional length that ranges from about 0.2 mm to about 1 mm. In other configurations, the diameter or cross-sectional length of the gate 78a-d can range from about 0.3 mm to about 0.9 mm or about 0.4 mm to about 0.8 mm. More specifically, configuring gate 78a-d can allow for a user to fabricate molded articles with a precise amount of polymer molecule orientation for structural fitness and function as an implantable plate.

In any event, the thermoplastic material will flow through gate region 76a-d and through each corresponding gate 78a-d before being introduced into a mold cavity 80a-d. The cavity 80a-d can be configured to be a void within the mold 52, and can be formed without any protrusions or flow disrupting formations.

Previously, injection molding systems have utilized various protrusions or features that extend through the mold cavity and result in flow directors that disrupt the polymer molecule orientation or cause eddies within the thermoplastic flow. The protrusions or other features that extend through the mold cavity have been used to create holes within such molded plates for receiving screws or other fasteners to secure the plate to the bone. However, the use of protrusions extending through the cavity have provided for structural problems within the molded articles because as the flow of material moves around each pin it comes together to form a joint line. Such joint lines are well known to be a source of fatigue and ultimate catastrophic failure when the plates are being used. The formation of joint lines or dwelt lines within a molded plate is unfavorable, and avoided by a cavity that does not include such features or pins that disrupt the thermoplastic flow. By having an open mold cavity, a molded plate can be fabricated with proper polymeric orientation to provide a strong and bendable implantable plate, as described in more detail below.

Additionally, in order to eliminate the pressure that can build up within a cavity 80 by the front of a thermoplastic flow, the cavities 80a-d can include a plurality of air vents 82a-e. Such air vents 82a-e are usually small in size so that air within the cavity 80a-d can be removed without a significant portion of the thermoplastic melt also flowing therethrough. Alternatively, the air vents 82a-c can have a substantial dimension in order to allow the flow of material to pass through, which can enhance the uniform polymer molecule orientation and result in a strong and bendable molded plate.

While one embodiment of an injection mold has been illustrated and descried, various other configurations and orientations of well-known injection molds can be employed. For example, the injection molding apparatus 50 can be comprised of a two body or three body mold, and can be operated with cold or hot runners. Additionally, various modifications can be made to the exemplary mold described herein.

V. Gate Design

In one embodiment of the present invention, an injection mold can be designed with gates that direct and orient the polymeric molecules in a manner that provides the strength and flexibility characteristics as described. More specifically, the gate dimensions and shapes can be optimized in order to provide directional alignment for a certain percentage of the polymer molecules. As such, the gates can be designed to cooperate with the polymer composition, thermoplastic flow rate, and other injection molding parameters in order to prepare an implantable plate with the strength for such use and the ability to flex or bend the plate so as to conform to the shape of the underlying bone. Exemplary gate designs are for providing polymer molecule orientation are described in more detail below.

FIGS. 3A-F illustrate embodiments of a gate 100a-f that can be used within the injection mold 50 of FIG. 2. Such gates 100a-f are configured to provide the proper orientation of the polymer molecules within the thermoplastic composition and the resulting implantable plate. With that said, the various embodiments of the gates will be described below.

Figure 3A:
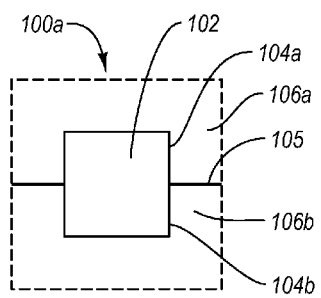
FIGS. 3A-F are cross-sectional schematic diagrams illustrating embodiments of injection mold gates in accordance with the present invention.

FIG. 3A depicts one embodiment of a gate 100a, which cooperates with a thermoplastic composition in order to provide proper orientation to the polymeric molecules. As such, gate 100a includes a gate aperture 102 that is defined by a first gate wall 104a of a first mold body 106a and a second gate wall 104b of a second mold body. When the first mold body 106a and the second mold body 106b come together to form a mold body junction 105, a uniform gate wall 104a-b is formed to define the gate aperture 102. While a square gate aperture 102 bisected by the mold body junction 105 is illustrated and described herein, various other shapes, conformations, and orientations can be utilized. Also, various dimensions and other aperture surface areas can be used in order to provide the proper orientation of the molecules; especially a narrowing or expanding gate region on either side of the gate aperture 102.

Figure 3B:
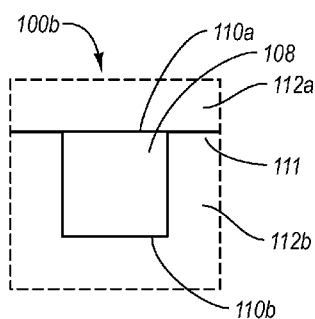

FIG. 3B depicts one embodiment of a gate 100b, which includes a gate aperture 108 that is defined by a first gate wall 110a of a first mold body 112a and a second gate wall 110b of a second mold body 112b. Accordingly, when the first mold body 112a comes together with the second mold body 112b to form a mold body junction 111, the first gate wall 110a comes together and joins with the second gate wall 110b to define the gate aperture 108. In this embodiment, the mold body junction 111 is on one end of the gate aperture 108 so as to illustrate that the orientation and/or placement of the gate aperture 108 with respect to the first mold body 112a and the second mold body 112b can be varied and still provide the proper orientation to the polymeric molecules.

Figure 3C:
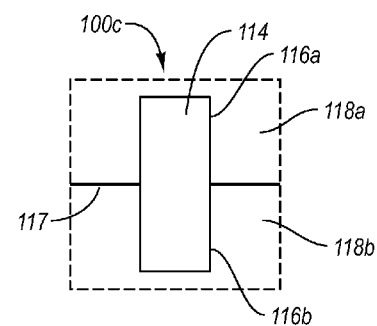

FIG. 3C depicts one embodiment of a gate 100c which includes a gate aperture 114 having a narrow and vertical orientation. The gate aperture 114 is defined by a first gate wall 116a of a first mold body 118a and a second gate wall 116b of a second mold body 118b. When the first mold body 118a and second mold body 118b form the mold body junction 117, the first gate wall 116a and second gate wall 116b cooperate to define the narrow and vertical gate aperture 114. A narrow vertical orientation can be preferred in some instances to provide increased polymer molecule orientation. As such the dimensions of gate aperture can be changed to have different sizes or cross-sectional areas in order to provide the proper polymer molecule orientation.

Figure 3D:
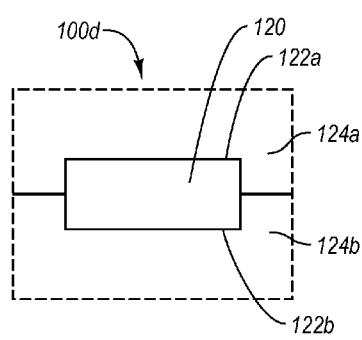

FIG. 3D depicts one embodiment of a gate 100d that includes a gate aperture 120 that is characterized by having a substantially horizontal cross-sectional area that is bisected by a first mold body 124a and a second mold body 124b. More specifically, the gate aperture 120 is defined by a first gate wall 122a, and the second gate wall 122b. As before, when the first mold body 124a comes together with the second mold body 124b, the first gate wall 122a cooperates with the second gate wall 122b in order to perform the gate aperture 120. A wide gate aperture 120 can be preferred in order to provide lower polymer molecule orientation.

Figure 3E:
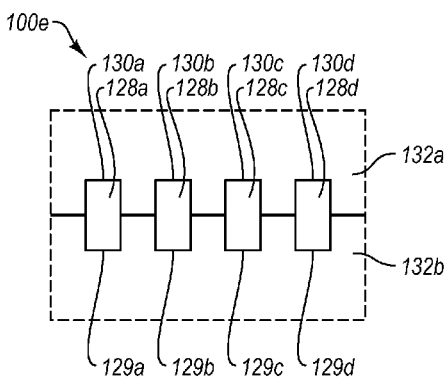

FIG. 3E depicts one embodiment of a gate aperture system 100e that is characterized by having a plurality of gate apertures 128a-d. As such, in place of a single gate aperture, a plurality of gate apertures 128a-d can be utilized to provide the proper polymer molecule orientation. Similar with the foregoing gate apertures, the gate aperture 128a is defined by a first gate wall 130a of a first mold body 132a and a by a second gate wall 129a of a second mold body 132b. Similarly, the gate apertures 128b-d are defined by the first gate walls 130b-d of the first molded body 132a and by the second gate walls 129b-d of the second mold body 132b. While a four aperture gate system 100e is illustrated and described, various other numbers of apertures can be used to provide the proper polymer molecule orientation.

Figure 3F:
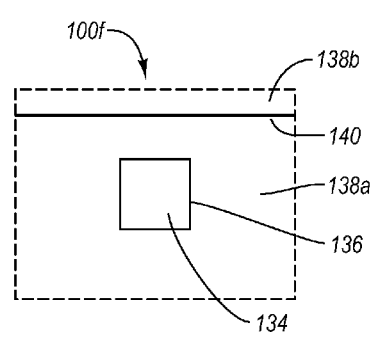

FIG. 3F depicts one embodiment of a gate 100f that includes a gate aperture 134 oriented within a first mold body 138a. As such, the gate aperture 134 includes a gate wall 136 which is completely defined by first mold body 138a. While mold body junction 140 separates the first mold body 138a from the second mold body 138b, it does not define any portion of gate aperture 134. This gate configuration allows for unique gate aperture orientations and placement with respect to the mold cavity. Also, by orienting the gate aperture within only one molded body the polymer molecule orientation can be enhanced for certain embodiments.

While various shapes, orientations, and configurations of gates 100a-f have been illustrated in FIGS. 3A-F, various changes to the dimensions, cross-sectional area, shape, and number of the apertures can be made in accordance with the present invention. This allows for a mold to be prepared with unique shapes and/or sizes that cooperate with the thermoplastic polymer compositions and flow rates in order to obtain proper polymer molecule orientation within the finished molded article. Examples of some cross-sectional shapes include circles, rectangles, squares, octagons, pentagons and the like, wherein various polygons can be used in order to provide the proper polymer molecule orientation. Additionally, a gate aperture diameter or cross-sectional length from about 10% to about 60% of the mold cavity average cross-sectional length (diameter) or runner cross-sectional length (diameter) can provide optimal polymer orientation. In other configurations the gate aperture diameter or cross-sectional length can range from about 20% to about 50% or from about 30% to about 40% of the mold cavity average cross-sectional length (diameter) or runner cross-sectional length (diameter).

In one embodiment, any of the gates 100a-f described herein can be fabricated as an independent component, or with a corresponding gate region, that can be removably inserted into an injection mold. That is, a single injection mold can be configured to include and/or receive interchangeable gates and/or gate regions. This allows for an injection mold to be modified between molding procedures in order to alter the polymer molecule orientation. As such, a predetermined gate and polymeric composition combination that provides the proper polymer molecule orientation can be utilized together during a molding procedure. As such, various other modifications to the foregoing embodiments of a gate can be made within the scope of the present invention as long as proper orientation of the polymeric molecules within a specific polymeric composition can be obtained.

VI. Molded Bodies

In one embodiment, the foregoing processes and systems can be employed to prepare molded bodies that include at least one portion configured to be an implantable plate. Additionally, the molded bodies are generally shaped to conform to the features of the mold cavity from which they were prepared. Exemplary molded bodies are discussed in more detail below.

Figure 4A:
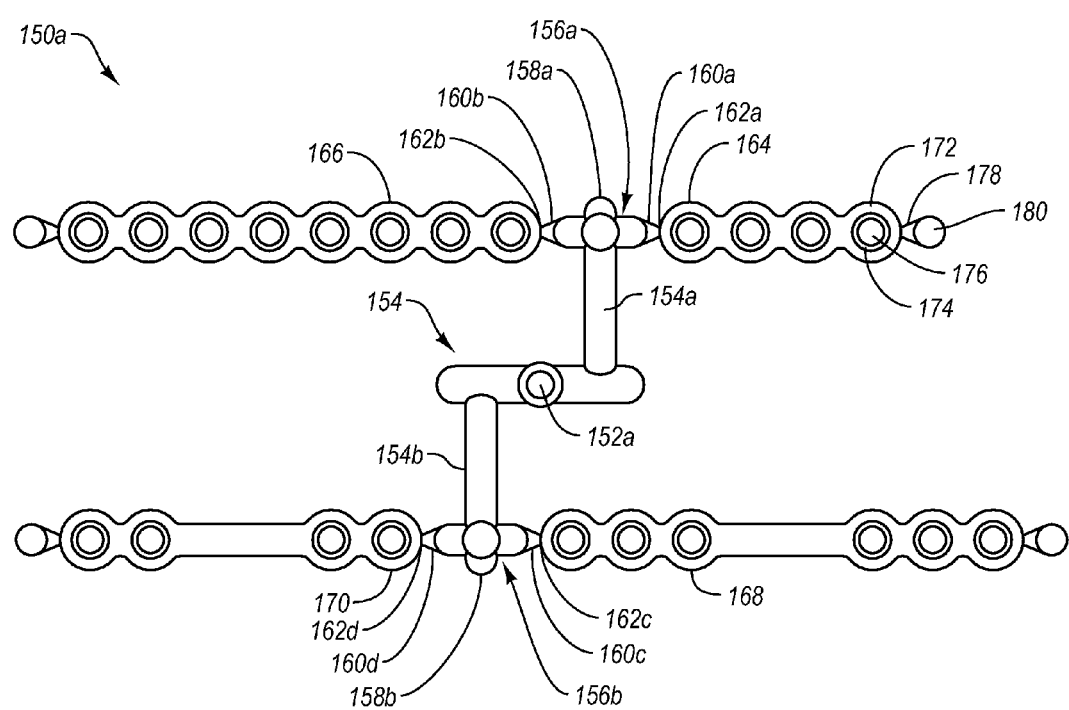
FIGS. 4A-C are top views illustrating embodiments of molded bodies in accordance with the present invention.
Figure 4B:
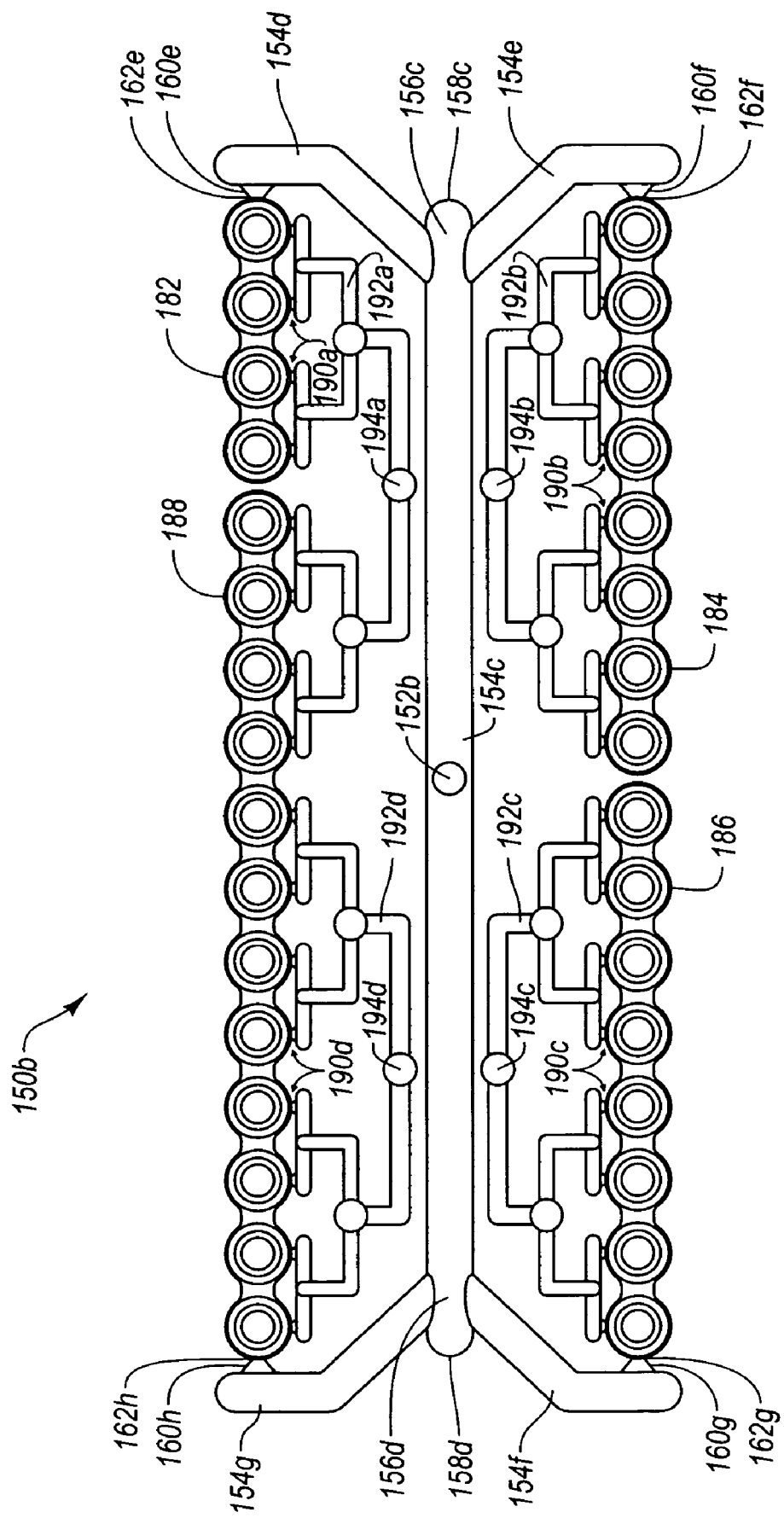
Figure 4C:
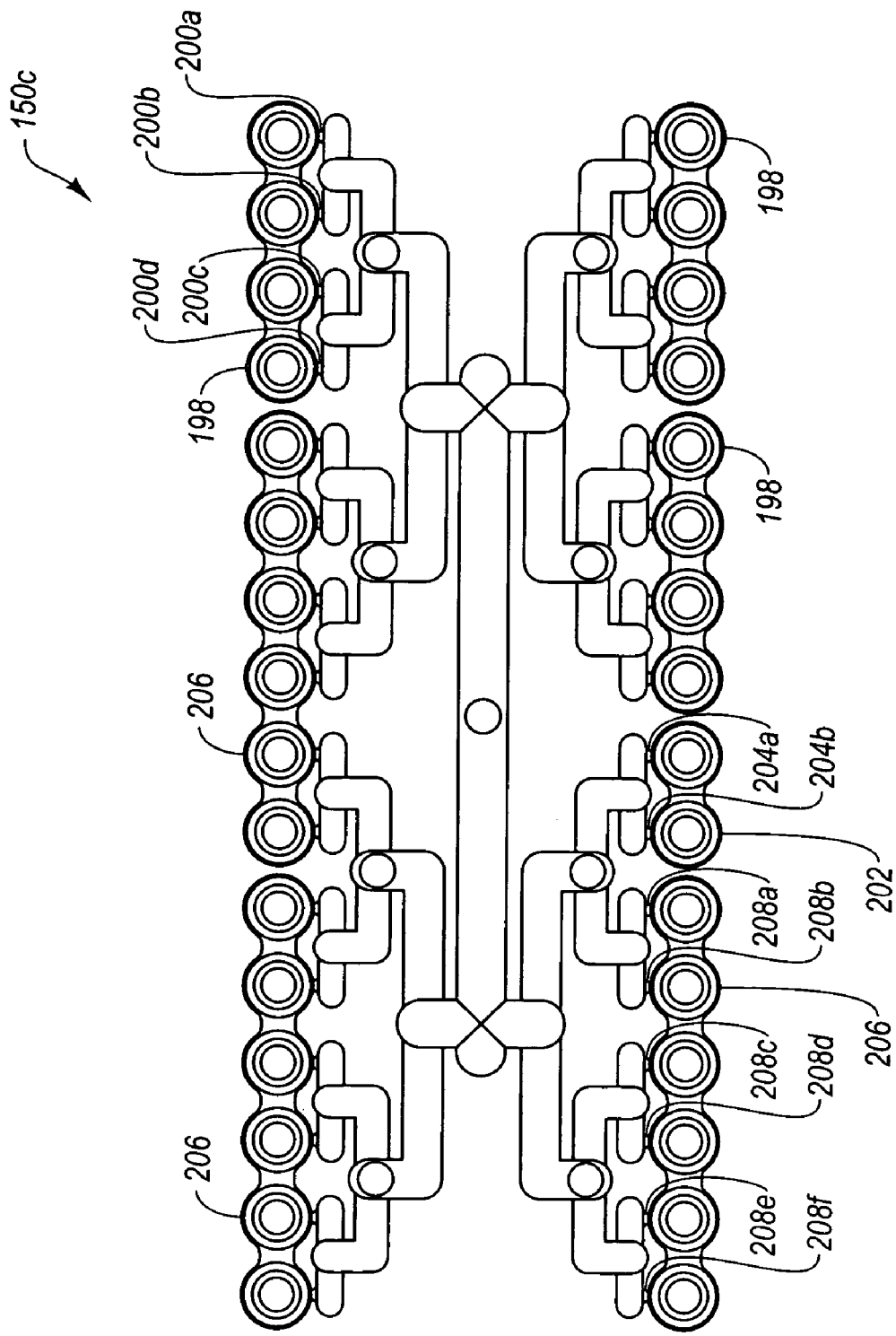

FIGS. 4A-C illustrate various embodiments of molded bodies 150a-c prepared in accordance with the present invention. More particularly, the molded bodies 150a-c are prepared by an injection mold 50 of FIG. 2. Accordingly, the injection mold 50 of FIG. 2 can be configured so that the cavities 80, runners 68, and the like provide the shapes and features shown on each of the molded bodies 150a-c described herein. Additionally, the cavity that forms the molded body 150a-c is devoid of any features that would separate the thermoplastic flow and allow for it to rejoin and form joint lines, which is shown by the plate body 172 being devoid of any holes as will be discussed below.

With specific reference now to FIG. 4A, a molded body 150a is illustrated and described. Such a molded body 150a includes a runner inlet 152a and runner network 154 comprised of runners 154a-b, which can be formed by the runner in the mold solidifying with the polymeric composition. Additionally, each runner 154a-b terminates at a runner divider 156a-b that is adjacent to a cold well 158a-b. Also, each runner divider 156a-b portion of the molded body 150a can be adjacent to a gate region 160a-d that includes a gate 162a-d. Each gate 162a-d can be connected to a plate body 172, which can be the 4-lock plate 164, 8-lock plate 166, 6-lock plate 168, and 4-lock plate 170. Additionally, each plate body 172 can be comprised of a plate recess 174 and hole template 176, and can be also connected to a vent 178 that formed from the thermoplastic flow entering a cold well 180. In some instances, the recess can be the hole template. Thus, the injection mold that fabricates the mold body 150a includes each and every feature that is depicted.

Additionally, the plate body 172 can be devoid of holes configured for receiving a fastener, which indicates that the corresponding mold can be also devoid of pins or protrusions extending through the cavity that would form such fastener holes. This is because the injection mold and mold cavity are configured to receive the thermoplastic flow in a manner that does not form joint lines. Thus, the cavity has an open configuration that inhibits joint formation by not having any features that separate the thermoplastic flow and allow for two cooled fronts to join back together.

FIG. 4B illustrates another embodiment of a molded body 150b that includes various features provided by a mold. As before, the molded body 150b includes a runner inlet 152b and a runner network 154 comprised of a plurality of runners 154c-g. Additionally, the molded body includes dividers 156c-d adjacent to the cold wells 158c-d, and a plurality of gate regions 160e-h and gates 162e-h at the ends of the runner network 154.

The molded body 150b also includes a 4-lock plate 182, 8-lock plates 184 and 186, and 12-lock plate 188 connected to the gates 162e-h. In contrast to molded body 150a that includes one vent 178 and one cold well 180 for each plate body 182-188, molded body 150b includes a plurality of vents 190a-d for each plate body 182-188. Additionally, each of the plurality of vents 190a-d opens into a cold well network 192a-d that has an air vent 194a-d.

Accordingly, the molded body 150b can be formed by the thermoplastic melt flowing into the cavity as with 150a. Additionally, the presence of the plurality of vents 190 for each plate body 182-188 that opens into a cold well network 192 allows for the thermoplastic melt to flow through the cavity without pressure building up. As such, the air escapes through the vent 190 via the cold well network 192 and out through the air vents 194. This configuration allows the thermoplastic flow to fill the cavity as well as the cold well network 192 as shown. In part, this configuration along with a properly designed gate 162 allows for proper polymer molecule orientation as described herein.

FIG. 4C depicts another embodiment of a molded body 150c, which includes many of the features described in connection with molded bodies 150a and 150b. Additionally, the molded body 150c can be configured into a non-bendable or non-degradable implantable plate. Molded body 150c differs by having a plurality of gates for each plate body as shown. As such, the 4-lock plate 198 includes a 4-gate system 200a-d; the 2-lock plate 202 includes a 2-gate system 204a-b; and the 6-lock plate 206 includes a 6-gate system 208a-f. In this configuration each cavity that forms a plate includes a plurality of gates so that the thermoplastic melt can enter each mold cavity at various locations. This mold configuration differs from including pins or other flow diverting features because the plurality of gates allow for the proper orientation of the polymeric molecules. When the polymer enters the cavity at various locations, minimal to no joints form because of the open-void nature of the cavity, which provides for homogenous distribution and proper orientation of the polymeric molecules.

While various features and embodiments of molded bodies have been described in connection herewith the FIGS. 4A-C, various other features and embodiments can be used. As such, molded bodies can be altered or changed to have various shapes and conformations and not depart from the spirit and scope of the present invention. Additionally, FIGS. 4A-C not only depict and describe molded bodies, but also the requisite features of mold in order to provide such molded bodies.

Figure 5:
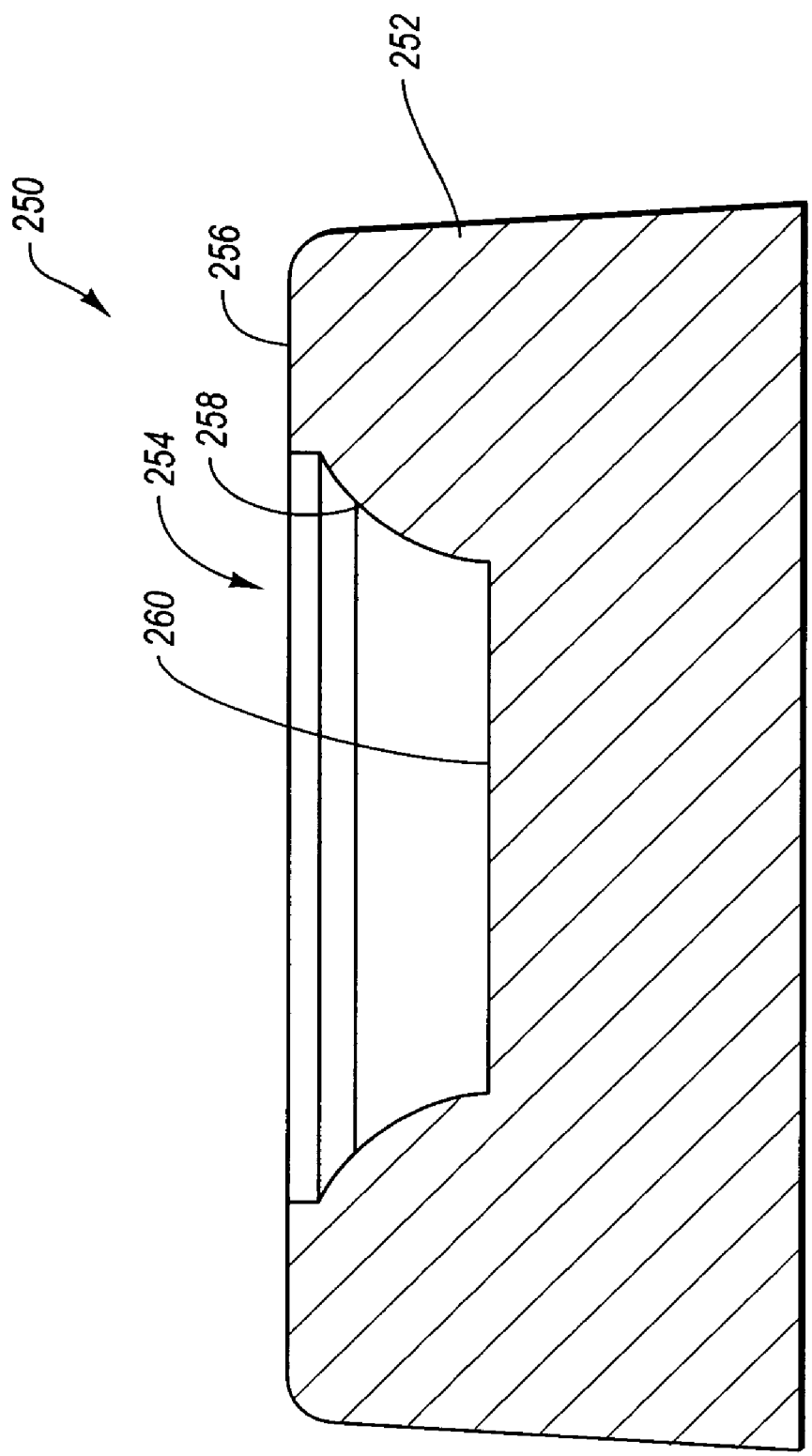
FIG. 5 is a cross-sectional view illustrating an embodiment of a molded plate in accordance with the present invention.

Referring now to FIG. 5, certain features of an embodiment of a molded plate 250 are illustrated and described. The molded plate 250 can include the features as previously described in connection with FIGS. 4A-C. More specifically, the molded plate 250 can include a plate body 252 comprised of a plate surface 256, recess surface 258, and hole template 260. The recess surface 258 defines a recess 254 that includes the hole template 260 at its base. Accordingly, the plate recess 254 and plate surface 256 are configured be compatible with the shape of a screw bolt or other fastening means. That is, a screw or other fastener can precisely fit into a plate recess 254 so it does not protrude above and over the plate surface 256.

The hole template 260 can be included at the bottom of the plate recess 254 and has the proper size and orientation in order to be drilled so as to form a hole. Alternatively, the recess can be the hole template. Moreover, the hole template can be a raised portion, annular ridge, indicia, and the like with or without being at the base of a recess so long as the placement of the hole is demarked upon the body of the plate by the hole template. When a hole is formed into the hole template 260, it provides a conduit for a fastener to be inserted and affix the molded plate 250 to a bone of a subject.

While embodiments of molded bodies have been depicted and described in connection with the present invention, other molded bodies having the desired polymer molecule orientation can be used. This can include molded bodies without any of the foregoing features such as recesses and hole templates. As such, a generally shaped molded body without a recess or hole template can be prepared so that subsequent processing can form the recesses and/or fastener holes.

VII. Drilling Polymeric Plates

In one embodiment of the present invention, a process for preparing an implantable plate includes drilling or otherwise forming holes for receiving a fastener. In exemplary embodiments, the fastener holes are formed by drilling through the hole templates in the molded body. Alternatively, the fastener holes can be formed by drilling at any location on a plate. Additional details of drilling system are described in more detail below.

Figure 6:
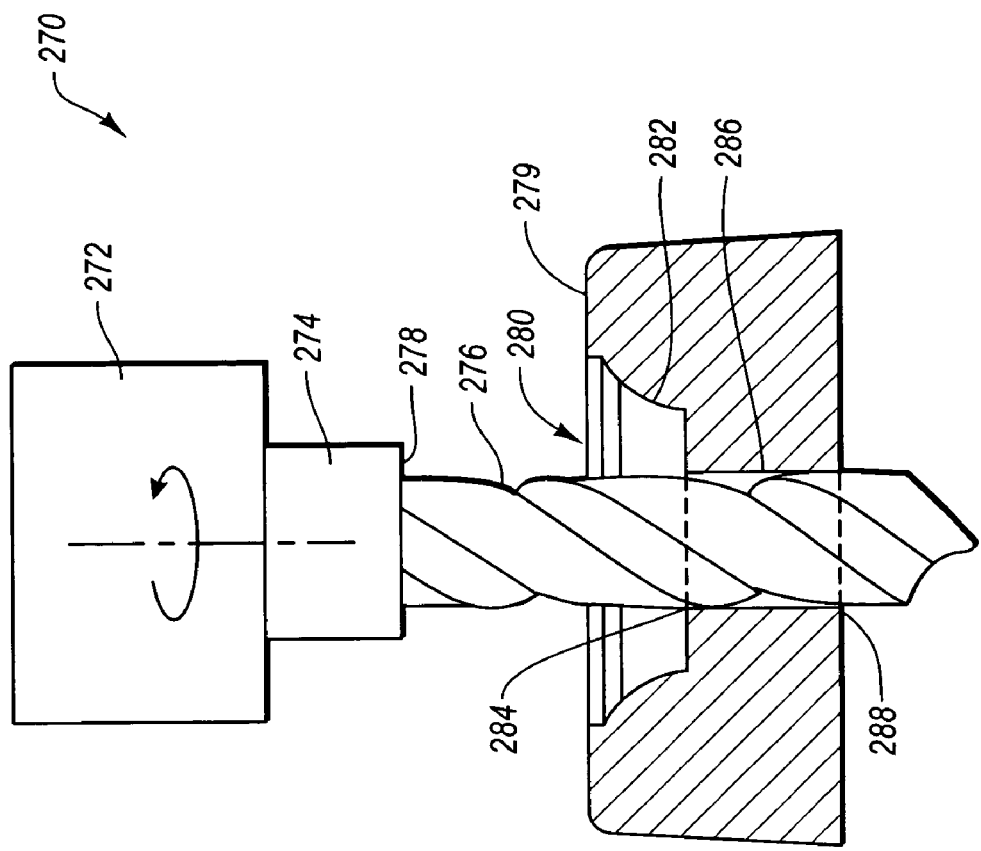
FIG. 6 is a cross-sectional view illustrating an embodiment of a drilling system in accordance with the present invention.

FIG. 6 depicts features of an embodiment of a drilling system 270 in accordance with the present invention. Such a drilling system 270 can be utilized within the drilling apparatus 28 of FIG. 1. The drilling system 270 can include a drilling device 272 configured to have the proper mechanics and components in order to provide the drilling functionality. As such, the drilling device 272 includes a drill bit holder 274 within the drill bit opening 278 configured hold a drill bit 276 while performing the drilling function. Additionally, drilling system 270 can include well-known automation in order to provide automated drilling.

As depicted, molded plate 279 includes a plate recess 280, which can be at least partially defined by the recess surface 282. This can provide for alignment and orientation of the drilling device 272, and more specifically, for the drill bit 276 to be aligned with respect to the bit entrance 284. The bit entrance 284 can be substantially the same as the hole template as previously described; however, the bit entrance 284 is the precise site that the drill bit 276 drills into to the molded body 279. Alternatively, the recess 280 or any portion of the molded plate 279 can be the hole template, and hence the bit entrance 284. The drill bit 276 then forms the hole 286 within the molded plate 279. After drilling completely through the molded plate 279, the drill bit 276 exits the bit exit 288. Thus, the drilling system 270 can form a hole 276 for receiving screws, bolts or other fastening means in order to fasten the molded plate to the bone of a subject.

In one embodiment, the automation can be used to orient and form the fastener holes. As such, a molded body without a recess or hole template can have fastener holes formed therein. That is, the automation can receive and/or orient the molded body in a position that enables the fastener holes to be drilled without any recess or hole template. This can include drilling a recess and/or drilling the fastener hole without any guidance provided by the molded body.

While one embodiment of a drilling system has been depicted and described, other drilling systems can be employed. Such drilling systems can include punching, milling, stamping, laser machining and like hold-forming equipment.

VIII. Implantable Polymeric Plates

In one embodiment of the present invention, the molded plates prepared by the foregoing systems and processes can be fabricated into implantable plates. Such implantable plates are usually separated from a general molded body before or after the fastener holes are formed. Additionally, the plate can be further processed as described herein in order to be properly finished for implantability. Exemplary plates are described in more detail below.

Figure 7:
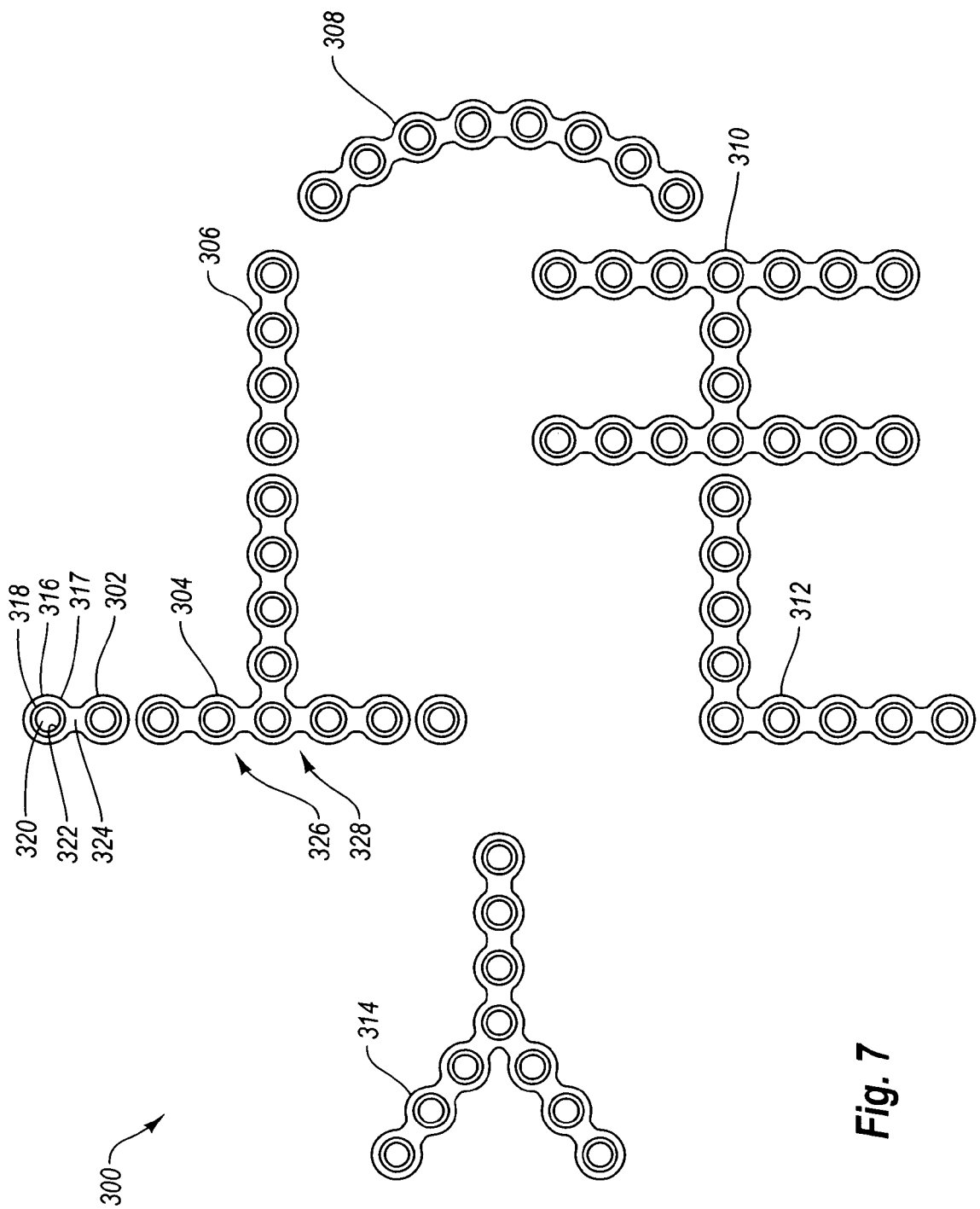
FIG. 7 is a top view illustrating embodiments of exemplary plates in accordance with the present invention.

With reference now to FIG. 7, various embodiments of exemplary implantable plates 300 are illustrated and described. Briefly, the plate fabrication system of FIG. 1 can produce the exemplary implantable plates 300. The exemplary implantable plates 300 are represented by a 2-lock plate 302, T-plate 304, 4-lock plate 306, arc-plate 308, H-plate 310, L-plate 312, and Y-plate 314. More details of the features of such exemplary plates 300 are provided below.

In one embodiment, each of the plates 302-314 can be defined by a plate body 316 comprised of a lock portion 317 and a spacer region 324. For example, the 2-lock plate 302 includes a lock portion 317 with a recess 318 adjacent with a fastener hole 320. The fastener hole 320 can be defined by a hole surface 322, and provides a conduit for receiving a fastener, such as a screw or bolt, in order to attach to the 2-lock plate 302 to the bone of a subject. Additionally, the spacer region 324 can be of any shape and dimension, and is not strictly limited to those illustrated and described herein. Also, the spacer region 324 can be extended to provide for any distance between respective fastener holes 320. Furthermore, some embodiments of plates 300 can include a junction region 328 that provides for the intersection of various arms 326, which can be exemplified by the T-plate 304, L-plate 312, and Y-plate 314.

While various plates with junctions 328 and arms 326 are illustrated and described, exemplary plates 300 can also be formed as rectangular plates, square plates, circular plates, and other polygonal shapes as well as custom or novel shapes. Additionally, the exemplary plates 300 can have any number of fastener holes 320 in any orientation or position. Thus, the plates of the instant invention are not limited in shape or size or fastener hole, and can be fabricated into any known or future developed implantable conformation.

Additionally, the foregoing implantable plates can be fabricated with biodegradable polymers in order to degrade slowly over time after being implanted. As such, the biodegradability of the plate can cause uniform degradation so as to avoid substantial shortening and/or shrinking of the dimensions of the plate. It is thought, without being bound to theory, that the biodegradability arises from water or other body fluid permeating into the implanted plate so as to soften the polymers and relax the orientation. Also, the designed polymer molecule orientation can aid in providing the biodegradability that does not result in the shorting and/or shrinking. For example, the biodegradable plate can degrade so that about 75% of the initial mass has degraded after about 10 months, more preferably after about 6 months, and most preferably after about months. This can also result in the plate fully degrading in about 14 months, more preferably about 1 year, and most preferably in about 10 months. Accordingly, the implantable plate can be configured to biodegrade so that the bone supports more weight in comparison to the implantable plate in less than 12 weeks, more preferably in less than 8 weeks, even more preferably less than 4 weeks, and most preferably after 2 weeks.

Also, the implantable plates can be configured to have a desired amount of polymer orientation that allows the plate to be bent up to an angle of about 45 degrees, or more if desired. In one embodiment, the plate can be configured to be bent to an angle up to or about 90 degrees without heat. In another embodiment, the plate can be configured to be bent without heat to an angle less than or about 45 degrees, or less than or about 35 degrees. In another configuration, the plate can be bent without heat to an angle less than or about 30 degrees. Alternatively, it can be preferred to have a more rigid plate that only bends up to or about 25 degrees, less than about 20 degrees, or less than about 15 degrees. In any event, the foregoing bendability can be achieved in the polymeric plates without the aid of any heat. That is, the plates can be bent without heating any portion of the plate and not causing any breakage such as fractures, cracks, deformations, or other structurally catastrophic malformations.

Furthermore, in order to achieve the bendability without any thermal energy, the polymer molecules can be oriented within the implantable plate to have a desired amount of orientation in substantially one direction. As used herein, the term "one direction" is meant to include polymers aligned in substantially one direction, but not necessarily entirely in only one direction. For example, when the polymer is biodegradable, such orientation includes less than about 40% of the polymer molecules oriented in substantially one direction. In another configuration, about 10% to about 30% or the polymer molecules can be oriented in substantially one direction, or about 15% to 25% oriented in substantially one direction.

In one embodiment, it can be preferred to prepare the implantable plate with a biodegradable polymer and another material such as an inert polymer, natural polymer, magnesium fiber, and/or silicon fiber. In one aspect, this can be beneficial to allow biodegradability over time and still retain some structural support after the degradable portion has been depleted. As such, this can be favorable for complex bone reconstructions that may need some long-term support. That is, an initially high amount of support can be provided that decreases over time until a final amount of support is obtained, which allows the bone to reform and strengthen as the biodegradable portion is depleted. Alternatively, additional biodegradable materials can enhance the biodegradability of the implantable plate. For example, the biodegradable polymer to other material ratio can range from about 10 to about 1, from about 8 to about 4 in other configurations, from about 6 to about 4 in yet other configurations, and vice versa depending on the characteristic desired Moreover, an embodiment of the implantable plate can be configured to minimally shrink in a water bath maintained at about 37° C. As such, the plate can be configured to have a dimension, such as length or width that shrinks less than about 6% of its original dimension in a period of 10 days, less than about 4% in other configurations, and less than 3% in still other configurations.

IX. Manufacturing Polymeric Plates

In one embodiment of the present invention, a method of manufacturing can produce an implantable plate having the features described in accordance with the present invention. Such a method of manufacturing can employ the foregoing compositions, equipment, systems, and processes as previously described. An exemplary method of manufacturing is described in more detail below.

Figure 8:
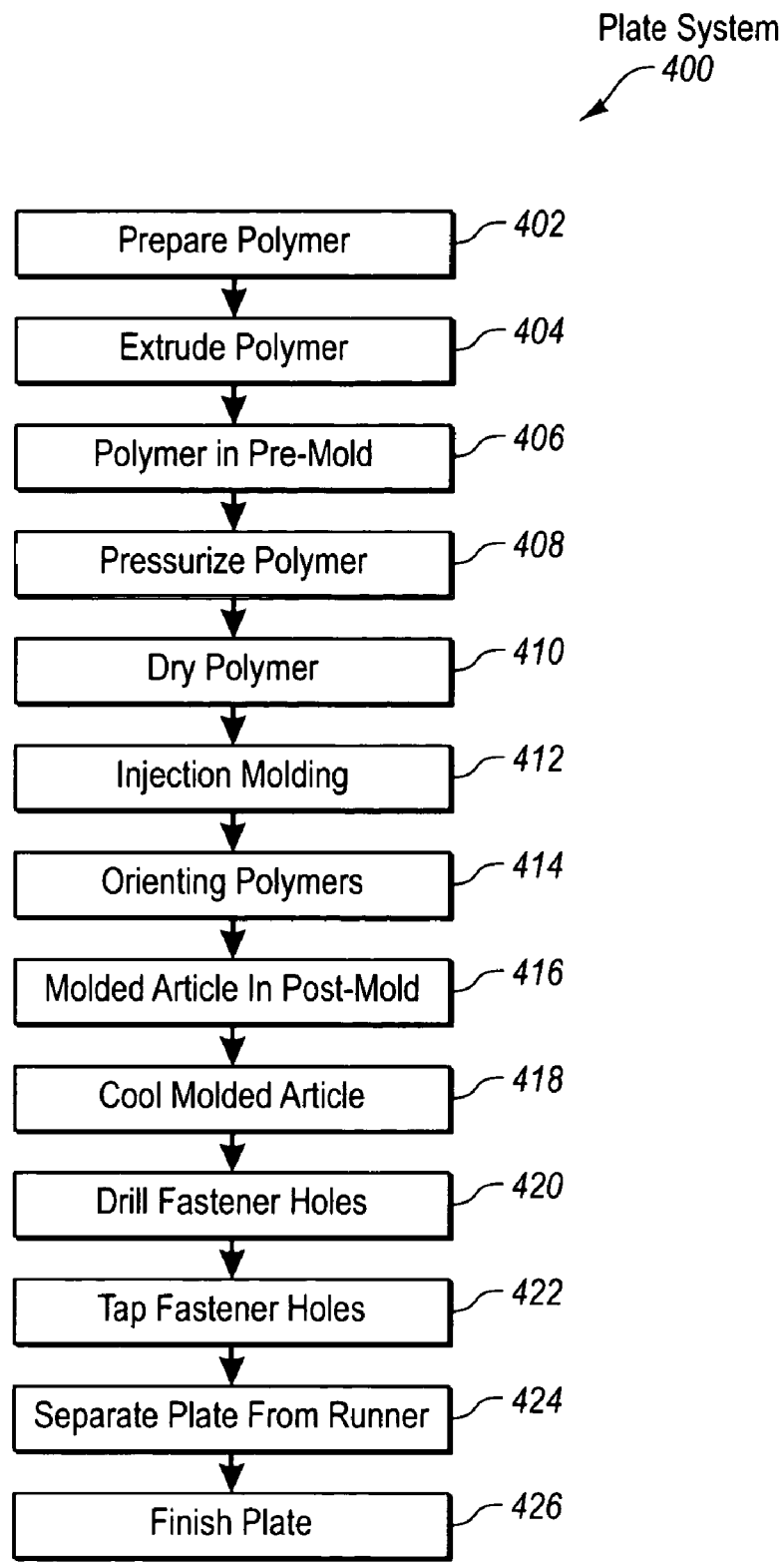
FIG. 8 is a flow diagram illustrating an embodiment of a method for fabricating a plate in accordance with the present invention.

FIG. 8 illustrates an embodiment of an implantable plate fabrication method 400. Such a plate fabrication method 400 can include and utilize any of the various equipment, components, and processes described in connection to FIG. 1 through FIG. 7. Accordingly, the plate fabrication method 400 includes preparing a polymer to have the thermoplastic characteristics and resulting plate strength and flexibility profiles as described above (402). By preparing the polymer composition to have the proper components and concentrations, the implantable plate can be prepared to have the preferred structural and flexibility features.

In one embodiment, the polymer composition can be extruded (404). Extruding the polymer composition can be beneficial in order to provide the proper configuration, consistency, temperature, and the like before injection molding. This can include further mixing and/or compaction of the polymeric materials as well as heating the polymer past its softening point, melting point, and/or glass transition temperature.

In any event, the polymer can be supplied into a polymer pre-mold (406). Within the pre-mold, the polymer composition can be pressurized so as to have the proper pressure for being injected into the injection mold (408). Additionally, the polymer composition can be dried in the pre-mold to remove any moisture (410).

After being properly conditioned, the polymer composition can be introduced into an injection mold for injection molding (412). Additionally, the polymer molecules in the composition can be oriented by a gate to have a desired amount of orientation (414). The injection molded body can then be moved into a post-mold (416). While in the post-mold, the molded body can be cooled for further processing (418).

Accordingly, after being substantially cooled and solidified, the plate fabrication method 400 can include drilling the fastener holes (420). Optionally, after fastener holes have been drilled into the molded article, the fastener holes can be tapped in order to have the proper threading in order to cooperate with any threaded bolt or screw used as a fastening means (422). Various known methods of using taps in order to form threaded holes can be used in connection therewith.

In one embodiment, either before or after the holes have been formed, the implantable plate can be separated from the polymeric runners or other polymeric features (424). More specifically, when the molded body is formed, which typically includes molded runners, vents, dividers, cold wells, and plate regions, the plate region can be separated for the other features. In any event, the separation can be performed by cutting, pressing, stamping, or otherwise removing the polymer features from the plates.

Moreover, after the plate has been separated from other polymeric features and drilled to provide fastener holes, the plate can be finished (426). Finishing can include grinding, surfacing, sanding or otherwise removing anomalies or other surface features on the molded plate. Also, the finishing can include providing a coating to the molded plate. Additionally, any other well-known process for finishing a molded article can be used in connection herewith in order to substantially finish the plate into a useable and implantable condition. Also, additional finishing may not be necessary because injection molding can prepare an implantable plate that is ready for use in a surgical procedure.

While certain features and embodiments of the present invention have been described, the present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A method of manufacturing an implantable plate for providing support to a bone of a subject when affixed thereto, the method comprising:
   providing a molten, substantially non-crystalline biocompatible polymeric composition that includes a plurality of polymeric molecules;
   exposing the molten, substantially non-crystalline biocompatible polymeric composition to a shear stress so as to align at least a portion of the polymeric molecules in substantially a polymer flow direction;
   injection molding the molten, substantially non-crystalline biocompatible polymeric composition in an injection mold cavity so as to form a polymeric body, wherein at least a portion of the polymeric body is configured to have a shape of an implantable plate at least partially defined by a top surface and bottom surface;
   removing the polymeric body from the injection mold; and
   forming at least one fastener hole within the implantable plate portion after being removed from the injection mold, wherein the at least one fastener hole extends from the top surface to the bottom surface.

2. A method as in claim 1, wherein the forming the at least one fastener hole includes drilling holes in the implantable plate portion.

3. A method as in claim 1, wherein the shear stress includes passing the molten, substantially non-crystalline polymeric composition through a gate that is configured for orienting the polymeric molecules in substantially the polymer flow direction.

4. A method as in claim 3, achieving the predetermined amount of polymeric molecule orientation in substantially the polymer flow direction further comprising:

configuring the injection mold to have at least one of a runner, a runner network, a flow divider, a cold well, a gate region, mold cavity orientation, vents, or mold temperature; and manipulating at least one of the runner, the runner network, the flow divider, the cold well, the gate, the gate region, mold cavity orientation, the vent, mold temperature, polymer composition, and polymer flow rate so as to achieve the predetermined amount of polymeric molecule orientation.

5. A method as in claim 3, further comprising configuring the gate to have at least one aperture that imparts the shear stress to the molten, substantially non-crystalline polymeric composition passing through the gate, wherein the at least one aperture is pre-designed to achieve a predetermined amount of polymeric molecule orientation in substantially the polymer flow direction.

6. A method as in claim 5, wherein the at least one aperture has a cross-sectional length from about 10% to about 60% of at least one of an average cross-sectional length of the cavity or a cross-sectional length of a runner.

7. A method as in claim 1, wherein the implantable plate is capable of being bent without heat to an angle of less than or about 90 degrees.

8. A method as in claim 7, wherein the implantable plate is capable of being bent without heat to an angle of less than or about 30 degrees.

9. A method as in claim 1, wherein the implantable plate shrinks less than about 6% of an original dimension when maintained in a fluid at 37° C. for 10 days.

10. A method as in claim 1, further comprising configuring the implantable plate to be biodegradable within a medium maintained at 37° C.

11. A method as in claim 1, further comprising configuring the implantable plate to biodegrade so that the bone supports more weight in comparison to the implantable plate after 6 weeks.

12. A method as in claim 1, wherein the predetermined amount of polymer molecule orientation includes more than about 10% and less than about 40% of the polymer molecules being oriented in substantially the polymer flow direction.

13. A method as in claim 1, further comprising configuring the injection molding to use a mold having a cavity that is substantially devoid of any pins or protrusions extending through the cavity so as to result in an implantable plate substantially devoid of joint lines.

14. A method as in claim 1, further comprising introducing fibers into the injection mold during the injection molding process so as to be encapsulated within the polymeric body, the fibers being selected from the group consisting of magnesium fiber, micro-porous silicon fiber, nano-porous silicon fiber, organic fiber, ceramic fiber, and combinations thereof.

15. A method as in claim 1, further comprising configuring a portion of the plate to be capable of delivering a drug after being implanted.

16. A method as in claim 15, wherein the portion is a polymeric coating on the plate.

17. A method as in claim 1, further comprising at least one of the following:

mixing the polymeric composition in a mixer;

extruding the polymeric composition as a thermoplastic extrudate;

heating the polymeric composition before being introduced into the injection mold introducing the polymeric composition into the injection mold under pressure;

cooling the polymeric body after being removed from the injection mold;

drilling a fastener hole with at least one of a drill bit or a laser;

forming threads in a wall that defines the at least one fastener hole;

separating the implantable plate portion form the polymeric body;

finishing the implantable plate portion into an biocompatible implantable plate; or configuring the implantable plate to be biodegradable.

\* \* \* \* \*